(12) United States Patent
Kuhlman et al.

(10) Patent No.: US 8,580,725 B2
(45) Date of Patent: Nov. 12, 2013

(54) AEROSOL PRODUCT COMPRISING A FOAMING CONCENTRATE COMPOSITION COMPRISING PARTICULATE MATERIALS

(75) Inventors: Dennis Eugene Kuhlman, Middletown, OH (US); Timothy Woodrow Coffindaffer, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 834 days.

(21) Appl. No.: 11/726,457

(22) Filed: Mar. 22, 2007

(65) Prior Publication Data

US 2007/0225193 A1    Sep. 27, 2007

Related U.S. Application Data

(60) Provisional application No. 60/784,787, filed on Mar. 22, 2006.

(51) Int. Cl.
*C11D 3/00* (2006.01)

(52) U.S. Cl.
USPC .......................... 510/276; 510/370; 510/426

(58) Field of Classification Search
USPC ............................. 510/276, 370, 426; 95/148
See application file for complete search history.

(56) References Cited

U.S. PATENT DOCUMENTS

| | | | |
|---|---|---|---|
| 3,121,517 A | | 2/1964 | Geary et al. |
| 3,773,064 A | | 11/1973 | Focht |
| 3,910,848 A | | 10/1975 | Froehlich et al. |
| 3,929,678 A | | 12/1975 | Laughlin et al. |
| 4,019,657 A | * | 4/1977 | Spitzer et al. ................. 222/136 |
| 4,326,052 A | | 4/1982 | Kang et al. |
| 4,326,053 A | | 4/1982 | Kang et al. |
| 4,377,636 A | | 3/1983 | Kang et al. |
| 4,385,123 A | | 5/1983 | Kang et al. |
| 4,557,853 A | | 12/1985 | Collins |
| 4,976,953 A | | 12/1990 | Orr et al. |
| 5,011,681 A | | 4/1991 | Ciotti et al. |
| 5,104,646 A | | 4/1992 | Bolich, Jr. et al. |
| 5,106,609 A | | 4/1992 | Bolich, Jr. et al. |
| 5,624,666 A | | 4/1997 | Coffindaffer et al. |
| 5,756,081 A | | 5/1998 | Wdowik |
| 5,840,789 A | | 11/1998 | Verstrat et al. |
| 5,975,378 A | | 11/1999 | Bayer |
| 5,990,233 A | | 11/1999 | Barron et al. |
| 6,063,366 A | * | 5/2000 | Sugai et al. ..................... 424/69 |
| 6,087,310 A | * | 7/2000 | Henkel ........................ 510/138 |
| 6,303,556 B1 | * | 10/2001 | Kott et al. ..................... 510/357 |
| 6,309,657 B2 | * | 10/2001 | Vatter et al. ................... 424/401 |
| 6,394,321 B1 | | 5/2002 | Bayer |
| 6,433,061 B1 | | 8/2002 | Marchant et al. |
| 6,635,702 B1 | | 10/2003 | Schmucker-Castner et al. |
| 7,235,230 B2 | * | 6/2007 | LeGrow et al. ............ 424/70.121 |
| 2002/0039561 A1 | * | 4/2002 | Doughty et al. ................. 424/59 |
| 2003/0086888 A1 | * | 5/2003 | LeGrow et al. ............. 424/70.12 |
| 2005/0183207 A1 | | 8/2005 | Chan et al. |
| 2006/0239953 A1 | | 10/2006 | Clapp et al. |

FOREIGN PATENT DOCUMENTS

WO    WO-00/76461 A2    12/2000

OTHER PUBLICATIONS

International Search Report, PCT Application No. PCT/US2007/007173, dated Sep. 18, 2007 (6 pages).
Paul A. Sanders, Principles of Aerosol Technology, p. 314 (Van Nostrand Reinhold Co. 1970).
C.D. Vaughn, "Solubility Effects in Product, Package, Penetration and Preservation" 103 Cosmetics and Toiletries 47-69, Oct. 1988.
C.D. Vaughn, "Using Solubility Parameters in Cosmetics Formulation" 36 J. Soc. Cosmetic Chemists, pp. 319-333, Sep./Oct. 1988.

* cited by examiner

*Primary Examiner* — Liam Heincer
*Assistant Examiner* — M. Reza Asdjodi

(57) ABSTRACT

An aerosol product comprises a foaming concentrate composition that comprises a surfactant and particulate material having a particle size of at least about 100 μm. The foaming concentrate composition and propellant are contained in a package comprising a container and a powder valve comprising an orifice having an orifice diameter of at least about 660 μm. Preferably, a ratio of the maximum particle size of the particulate material to the orifice diameter of the orifice is less than about 0.75.

1 Claim, 1 Drawing Sheet

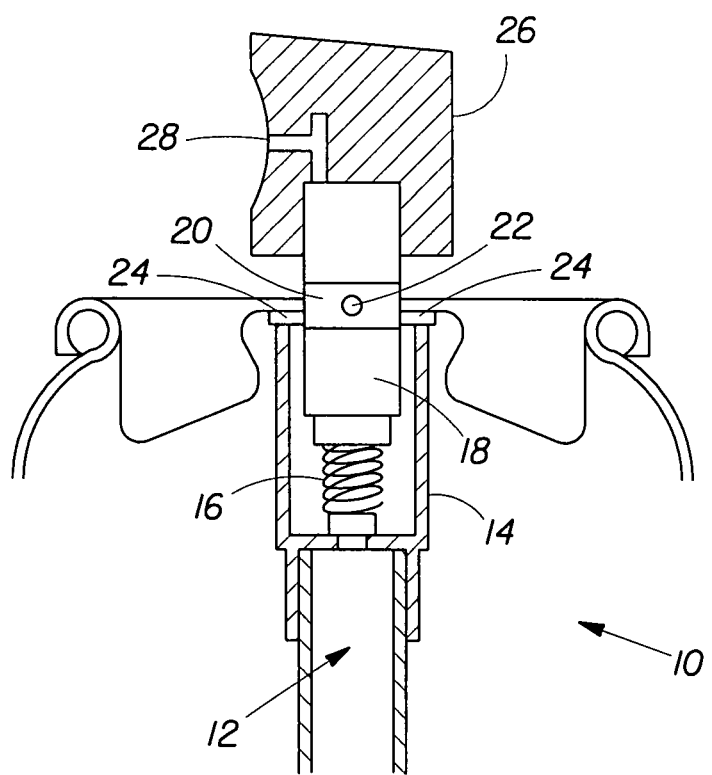

AEROSOL PRODUCT COMPRISING A FOAMING CONCENTRATE COMPOSITION COMPRISING PARTICULATE MATERIALS

CROSS REFERENCE TO RELATED APPLICATIONS

This application claims the benefit of U.S. Provisional Application Ser. No. 60/784,787 filed on Mar. 22, 2006 entitled "Aerosol Product Comprising A Foaming Concentrate Composition Comprising Particulate Materials".

FIELD OF THE INVENTION

The present invention relates to foaming aerosol products comprising particulate materials that are dispensed from a package comprising a powder valve.

BACKGROUND OF THE INVENTION

Personal care and household care compositions that comprise relatively large particles are becoming more popular. Personal care compositions comprise larger particles, such as polyethylene beads, to provide skin exfoliation benefits or skin feel benefits. Household care compositions comprise larger particles to scrub soils from hard surfaces, such as dishes. Such products also typically generate foam to assist in cleansing the surface being treated with the composition.

Such compositions are typically dispensed from hand pump packages by manually actuating the hand pump, or dispensed from bottles by manually squeezing the bottle. After dispensing, it is then generally required to add water and manually manipulate the compositions to generate foam or lather so that the composition can be used to cleanse the surface being treated.

Aerosol packages are a way to generate copious amounts of foam from a foaming composition upon dispensing, however attempting to deliver a foaming product with relatively large particulate materials in an aerosol product can result in a clogged or seeping valve, rendering the product useless. The historical limit on maximum particle size of particulate material that can be dispensed through aerosol valves has been 100 microns ($\mu m$) and for most products the particle size should be below 50 $\mu m$. See, e.g., Paul A. Sanders, PRINCIPLES OF AEROSOL TECHNOLOGY, pg. 314 (Van Nostrand Reinhold Co. 1970).

It has thus been desired to develop a product comprising relatively large particulate materials that can generate foam upon dispensing.

SUMMARY OF THE INVENTION

The present invention relates to an aerosol product that comprises a foaming concentrate composition and a propellant contained in a package comprising a powder valve and a container. The foaming concentrate composition comprises at least about 0.1%, by weight of the foaming concentrate composition, of particulate material having a particle size of at least about 100 $\mu m$. The powder valve comprises an orifice having an orifice diameter of at least about 0.026 inches (660 $\mu m$). Preferably, a ratio of the maximum particle size of the particulate material to the orifice diameter is less than about 0.75. The present invention provides a cleansing composition that foams upon dispensing and contains relatively large particulate material to provide benefits such as skin exfoliation or hard surface scrubbing, while avoiding clogging or seeping of the aerosol valve.

BRIEF DESCRIPTION OF THE DRAWING

The FIGURE is a side elevational view in partial section of an assembled powder valve mounted to a container of the present invention.

DETAILED DESCRIPTION OF THE INVENTION

Foaming Concentrate Compositions

The aerosol product of the present invention comprises a foaming concentrate composition for cleaning a variety of surfaces, such as skin, hair, or hard surfaces such as dishes, floors or the like. The foaming concentrate composition comprises surfactant and at least 0.1%, by weight of the foaming concentrate composition, of particulate material having a particle size of at least about 100 $\mu m$. The foaming concentrate composition can further comprise a number of optional ingredients.

Preferably, the foaming concentrate of the present invention produces foam upon dispensing from a package containing the foaming concentrate, rather than requiring a consumer to generate foam by manually manipulating the foaming concentrate after dispensing (i.e. a post-foaming composition).

Particulate Materials

The foaming concentrate compositions of the present invention comprise from about 0.1% to about 10%, preferably from about 0.3% to 6%, more preferably from about 0.5% to about 3%, more preferably from about 1% to about 3%, and more preferably from about 1.5% to about 2.5%, by weight of the foaming concentrate composition, of particulate material. The foaming concentrate compositions of the present invention comprise at least about 0.1%, preferably at least about 0.25%, more preferably at least about 0.5%, and more preferably at least about 1%, by weight of the foaming concentrate composition, of particulate materials having a particle size of at least about 100 microns ($\mu m$), preferably at least about 150 $\mu m$, and more preferably at least about 200 $\mu m$. The larger size particulate materials can provide a variety of benefits in the present foaming concentrate compositions, such as skin exfoliation or hard surface scrubbing. In addition, the foaming concentrate compositions of the present invention can optionally further comprise particulate material having a particle size less than 100 $\mu m$. The particulate material of the present invention preferably has a maximum particle size of less than about 600 $\mu m$, preferably less than about 500 $\mu m$, more preferably less than about 400 $\mu m$, and more preferably less than about 350 $\mu m$. The maximum particle size of the particulate material can be measured based on passing through a sieve.

The particulate materials of the present invention can be derived from a wide variety of materials including those derived from inorganic, organic, natural, and synthetic sources. These particles are supplied in all different sizes and shapes which can have an impact on their ability to be used in an aerosol product. Particle size is typically controlled and/or measured via the ability of a particle to pass through a specific sieve size. The sieve will allow particles to move through as long as the particle is less than a specific size along one axis. In addition, different means of manufacture of beads, especially polymers (e.g., polyethylene or polypropylene) can influence the roughness of the particle. Thus one needs to understand not only the size and shape of the particle, but also the outside roughness of the particle as smoother particles tend to pass through the orifice(s) in the valve of the package of the present invention easier than rougher particles. The ratio of maximum particle size of the particular material to the diameter of the orifice in the valve of the package can be particularly important to prevent the orifice from getting clogged with the particulate material. The ratio of maximum particle size to orifice diameter is generally less than about 0.75, preferably less than about 0.7, more preferably less than about 0.6, more preferably less than about 0.5, and more preferably less than about 0.4.

Non-limiting examples of particulate materials of the present invention include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are particles made from mixed polymers (e.g., copolymers, terpolymers, etc.), among such are polyethylene/polypropylene copolymer, polyethylene/propylene/isobutylene copolymer, polyethylene/styrene copolymer, and mixtures thereof. Typically, the polymeric and mixed polymeric particles are treated via an oxidation process to destroy impurities and the like. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, urea-formaldehyde resins, and the like. When such waxes and resins are used herein, they are solids at ambient and skin temperatures. Preferred particulate materials for use herein include polyethylene beads, polypropylene beads, and/or oxidized polyethylene beads. High density polyethylene or low density polyethylene can be used to make the preferred particulate materials of the present invention. High density polyethylene and polypropylene beads tend to have a rougher surface as compared to low density polyethylene beads. Examples of preferred particulate materials are available from Accutech under the trade name ACCUSCRUB; from Micropowder Inc. under the trade name PROPYLTEX 50; and from Honeywell under the trade name AC WAX 395-A.

Surfactants

The foaming concentrate compositions of the present invention comprise one or more surfactants, preferably a lathering surfactant. A lathering surfactant is defined herein as surfactant which generates foam or lather upon dispensing from an aerosol package. Preferably, these surfactants or combinations of surfactants should be mild, which means that these surfactants provide sufficient cleansing or detersive benefits but do not overly dry the skin or hair while still providing sufficient foam or lather.

A wide variety of lathering surfactants are useful herein and include those selected from the group consisting of anionic surfactants, nonionic surfactants, amphoteric surfactants, zwitterionic surfactants, and mixtures thereof. Generally, the lathering surfactants are fairly water soluble. When used in the foaming concentrate composition, preferably at least about 1%, by weight of total surfactant, of the surfactants have a HLB value greater than about 10. Examples of such surfactants are found in U.S. Pat. No. 5,624,666, to Coffindaffer et al., issued Apr. 29, 1997. Cationic surfactants can also be used, provided they do not negatively impact the overall lathering characteristics of the foaming concentrate composition.

The foaming concentrate composition comprises from about 1% to about 30%, preferably from about 2% to about 20%, more preferably from about 3% to about 10%, and more preferably from about 4% to about 8%, by weight of the foaming concentrate composition, of surfactant. To avoid potential skin irritation issues, the foaming concentrate compositions preferably have a ratio, by weight of the composition, of anionic surfactant to amphoteric and/or zwitterionic surfactant of from about 1.1:1 to about 1:1.5, alternatively from about 2:1 to about 1:2, and alternatively from about 5:1 to about 1:4.

Nonlimiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Nonlimiting examples of anionic surfactants include those selected from the group consisting of sarcosinates, sulfates, sulfonates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are soaps (i.e., alkali metal or amine salts, e.g., sodium, potassium or triethanol amine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps useful herein are described in more detail in U.S. Pat. No. 4,557,853. The degree of neutralization of fatty acids can vary and provide different foaming and lathering characteristics. Preferred soap-containing compositions have a pH between about 6 and about 7.5.

Suitable amphoteric or zwitterionic surfactants for use in the compositions herein include those which are known for use in hair care or other personal care cleansing. Such amphoteric or zwitterionic surfactants are typically present at a level of from about 1% to about 10%, alternatively from about 0.5% to about 20%, by weight of the foaming concentrate composition. Non-limiting examples of suitable zwitterionic or amphoteric surfactants are described in U.S. Pat. Nos. 5,104,646 and 5,106,609.

Amphoteric surfactants suitable for use in the present compositions are well known in the art and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric surfactants for use in the present invention are selected from the group consisting of cocoamphoacetate, cocoamphodiacetate, lauroamphoacetate, lauroamphodiacetate, and mixtures thereof.

Commercially available amphoteric surfactants include those sold under the trade names Miranol C2M Conc. N.P., Miranol C2M Conc. O.P., Miranol C2M SF, Miranol CM Special, Miranol Ultra (Rhodia, Inc.); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercoteric MS-2 (Scher Chemicals).

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Preferred zwitterionic detersive surfactants are the betaines, amphoacetates and sulfobetaines, e.g., cocoamidopropylbetaine, sodiumlaurylamphoacetate and cocoamidopropylhydroxysultaine.

Nonlimiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Nonlimiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

Preferred surfactants for use herein are the following: wherein the anionic surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, salts or partial salts of lauric acid or myristic acid and mixtures thereof; wherein the nonionic surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Suspension Agents

The present compositions optionally, but preferably, further comprise a suspension agent. A suspension agent can be important to suspend the particulate materials, such as oxidized polyethylene beads, in the present compositions to prevent the particles from falling out of solution or agglomerating in the composition. This further helps to prevent clogging of the aerosol valve. Thus a suspension agent can be important in achieving a composition that is stable and minimizes clogging of the aerosol valve.

When the present compositions are designed to be dispensed from an aerosol dispenser, it can be important to select a level and type of suspension agent that provides enough suspension for particulate materials, but at the same time is easily dispensible and foamable upon dispensing.

In this respect, the level and type of suspension agent is preferably selected to provide a non-Newtonian viscosity property. In this regard, the preferred suspension agents herein provide a shear-thinning composition that is capable of suspending particulate materials, such as oxidized polyethylene beads, in the composition matrix.

When present, suspension agents are typically included at a level of from about 0.001% to about 10%, preferably from about 0.005% to about 5%, and more preferably from about 0.01% to about 2%, by weight of the foaming concentrate composition.

The suspension agents herein can be selected from materials such as pectine, alginate, arabinogalactan, carageenan, gellan gum, xanthum gum, guar gum, acrylates/acrylic polymers, water-swellable clays, fumed silicas, acrylate/aminoacrylate copolymers, cellulose derivatives (e.g. hydroxypropylmethylcellulose), and mixtures thereof. Preferred suspension agents herein include those selected from the group consisting of acrylate/acrylic polymers, gellan gum, fumed silicas, acrylate/aminoacrylate copolymers, water-swellable clays, and mixtures thereof.

Acrylate/acrylic polymers include acrylic emulsion terpolymers. These types of dispersants are typically alkali activated. Suitable alkali activated acrylate/acrylic polymers are described in detail in U.S. Pat. Nos. 5,990,233 and 5,840,789. Such alkali activated acrylate/acrylic polymer dispersants are available from Alco Chemical under the trade name ALCOGUM® SL series.

Gellan gum is a heteropolysaccharide prepared by fermentation of Pseudomonaselodea ATCC 31461. Gellan gum is available from CP Kelco U.S., Inc. under various trade names, including KELCOGEL®, KELCOGEL® LT100, KELCOGEL® AFT, KELCOGEL® AF, KELCOGEL® PC, and KELCOGEL® F. Processes for preparing gellan gum are described in U.S. Pat. No. 4,326,052 (Kang et al), issued Apr. 20, 1982; U.S. Pat. No. 4,326,053 (Kang et al), issued Apr. 20, 1982; U.S. Pat. No. 4,377,636 (Kang et al), issued Mar. 22, 1983; and U.S. Pat. No. 4,385,123 (Kang et al), issued May 24, 1983.

Fumed silicas are a colloidal form of silica made by combustion of silicon tetrachloride in hydrogen-oxygen furnaces. Fumed silicas are known by the chemical name silicium dioxide. Fumed silicas suitable in the present compositions are available from Degussa AG under the tradename AEROSIL®. A preferred fumed silica is AEROSIL® 200 (available from Degussa AG), which is a hydrophilic fumed silica having a specific surface area of about 200 $m^2$/gram.

Acrylate/aminoacrylate copolymers are typically aqueous dispersions of an amine functional acrylic polymer rheology modifier. These types of dispersants are typically acid activated, as compared to acrylate/acrylic polymer dispersants described hereinbefore which are typically alkali activated. Acrylate/aminoacrylate copolymers are available from Alco Chemical under the trade name ALCOGUM® L-500 series. Another suitable acrylate/aminoacrylate copolymer is acrylates/aminoacrylates/C10-30 alkyl PEG-20 itaconate copolymer available from National Starch and Chemical Co. under the trade name STRUCTURE PLUS®.

Suitable clays include both natural and synthetic clays. Synthetic layered silicates are available from Southern Clay Products, Inc. under the trade name LAPONITE®. These synthetic layered silicates are layered hydrous magnesium silicates, in which magnesium ions, partially replaced by suitable monovalent ions such as lithium, sodium, potassium and/or vacancies, are octahedrally coordinated to oxygen and/or hydroxyl ions, some of which may be replaced by fluorine ions, forming the central octahedral sheet, the octahedral sheet being sandwiched between two tetrahedral sheets of silicon ions, tetrahedrally coordinated to oxygen. Preferred synthetic layered silicates include LAPONITE® XLG, LAPONITE® RD and LAPONITE® RDS available from Southern Clay Products, Inc. Hectorites are available from Rheox, Inc. under the trade name BENTONE®. These hectorites are prepared by reacting bentonite in a cation exchange system with an amine. Preferred hectorites include BENTONE® LT and BENTONE® AD available from Rheox, Inc. Further suitable materials include silicate materials such as OPTIGEL® series of materials available from Süd-Chemie, including OPTIGEL® WM, which is a mixture of bentonite (also known as montmorillonite) and xanthan gum, and the GEL WHITE® series of materials available from Southern Clay Products.

Other suitable suspension agents herein include anionic hydrophobically modified alkali-soluble acrylic polymers. Non-limiting examples of such polymers include the ACULYN® series of materials from Rohm and Haas, such as ACULYN® 28 (acrylates/beheneth-25 methacrylate copolymer) and ACULYN® 88 (acrylates/steareth-20 methacrylate crosspolymer).

Cross-linked acid copolymers, such as alkyl substituted acid copolymers, are also suitable suspension agents herein. One class of alkyl substituted copolymers include a rheology modifying copolymer containing a cross-linked copolymer selected from the group consisting of unsaturated carboxylic acid, a hydrophobic monomer, a hydrophobic chain transfer agent, a cross linking agent, a steric stabilizers and combinations thereof. Carbopol EDT 2020™ from Noveon™ is an example of this suspending agent. Details regarding such suspending agents are found in U.S. Pat. No. 6,433,061, Marchant et al., Aug. 13, 2002.

Another class of suitable suspension agents include a substantially cross-linked alkali-swellable acrylate copolymer as described in U.S. Pat. No. 6,635,702. CARBOPOL AQUA SF-1™ from Noveon™ is an example of this type of suspending agent. Another class of commercially available copolymers useful herein include copolymers of $C_{10\text{-}30}$ alkyl acrylates with one or more monomers of acrylic acid, methacrylic acid, or one of their short chain (i.e. $C_{1\text{-}4}$ alcohol) esters, wherein the cross linking agent is an allyl ether of sucrose or pentaerytritol. These copolymers are known as acrylates/$C_{10\text{-}30}$ alkyl acrylate cross polymers and are commercially available as Carbopol® 1342, Pemulen® TR-1, and Pemulen® TR-2, from Noveon™. Yet another class of copolymers include polymers that fall under the description of acrylates/vinyl alkyl cross polymers, commercially available as Stabylen® 30 from 3V, Inc.

The cross-linked maleic anhydride copolymers include cross linked $C_1\text{-}C_{10}$ alkyl vinyl ether/maleic anhydride copolymers. Stabileze QM™ from ISP Corporation is an example of this type of material. In order to be effective, the maleic anhydride segment of this copolymer needs to be at least partially neutralized so that the copolymer becomes anionic.

Particularly useful are cross-linked cross copolymers include cross-linked alkyl substituted acid copolymers and alkali-swellable acrylate copolymers.

Preferred suspension agents herein include synthetic layered silicates (e.g. LAPONITE® XLG), bentonite clays (e.g. OPTIGEL® WM), acrylates/C10-30 alkyl acrylate crosspolymer (CARBOPOL® AQUA SF-1), acrylates/beheneth-25 methacrylate copolymer (ACULYN® 28), acrylates/steareth-20 methacrylate crosspolymer (ACULYN® 88), hydroxypropylmethylcellulose, and mixtures thereof.

Hydrophobic Conditioning Agents

The compositions of the present invention optionally further comprise hydrophobic conditioning agents, especially when the composition is intended to cleanse and/or moisturize the skin or hair. The hydrophobic conditioning agents used herein are preferably natural or synthetic materials having an overall solubility parameter less than about 12.5 $(\text{cal/cm}^3)^{0.5}$, preferably less than about 11.5 $(\text{cal/cm}^3)^{0.5}$. By "overall solubility parameter" is meant that it is possible to use hydrophobic conditioning agents with solubility parameters higher than 12.5 $(\text{cal/cm}^3)^{0.5}$ if they are blended with other oils to reduce the overall solubility parameter of the oil mixture to less than about 12.5 $(\text{cal/cm}^3)^{0.5}$. For example, a small portion of diethylene glycol (sol par=13.61) could be blended with lanolin oil (sol par=7.3) and a co-solubilizing agent to create a hydrophobic conditioning agent that has a solubility parameter of less than 12.5 $(\text{cal/cm}^3)^{0.5}$.

Solubility parameters for the hydrophobic conditioning agents described herein are determined by methods well known in the chemical arts for establishing the relative polar character of a material. A description of solubility parameters and means for determining them are described by C. D. Vaughn, "Solubility Effects in Product, Package, Penetration and Preservation" 103 Cosmetics and Toiletries 47-69, October 1988; and C. D. Vaughn, "Using Solubility Parameters in Cosmetics Formulation", 36 J. Soc. Cosmetic Chemists 319-333, September/October, 1988.

The hydrophobic conditioning agents of the present invention typically comprise from about 2% to 15%, alternatively from about 1% to about 20% alternatively from alternatively from about 0.5% to about 30% and alternatively from about 0.1% to about 50% by weight of the composition. These materials include but are not limited to hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, dimethylpolysiloxane, diethylpolysiloxane, mixed $C_1\text{-}C_{30}$ alkyl polysiloxanes, phenyl dimethicone, dimethiconol, and combinations thereof. Preferred are non-volatile silicones selected from dimethicone, dimethiconol, mixed $C_1\text{-}C_{30}$ alkyl polysiloxane, and combinations thereof. Non-limiting examples of silicone oils useful herein are described in U.S. Pat. No. 5,011,681 (Ciotti et al.).

Non-limiting examples of diglycerides and triglycerides suitable for use herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof. In addition any of the above oils that have been partially or fully hydrogenated are also suitable.

Non-limiting examples of acetoglyceride esters suitable for use herein include acetylated monoglycerides.

Non-limiting examples of alkyl esters suitable for use herein include isopropyl esters of fatty acids and long chain esters of long chain fatty acids, e.g. SEFA (sucrose esters of fatty acids). Lauryl pyrolidone carboxylic acid, pentaerythritol esters, aromatic mono, di or triesters, and cetyl ricinoleate are non-limiting examples of which include isopropyl palmitate, isopropyl myristate, cetyl ricinoleate and stearyl ricinoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use herein include oleyl myristate, oleyl stearate, oleyl oleate, and combinations thereof.

Non-limiting examples of lanolin and lanolin derivatives suitable for use herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinoleate, hydroxylated lanolin, hydrogenated lanolin and combinations thereof.

Still other suitable oils include milk triglycerides (e.g., hydroxylated milk glyceride) and polyol fatty acid polyesters.

Still other suitable oils include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

Hydrophilic Conditioning Agents

The compositions of the present invention can optionally further comprise hydrophilic conditioning agents, especially in compositions for treating skin or hair. Non-limiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3-C6 diols and triols, alpha-hydroxy C2-C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the articles of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990.

When used in the present compositions, hydrophilic conditioning agents are present at a level of from about 0.1% to about 99%, preferably from about 0.25% to about 90%, more preferably from about 0.5% to about 10%, and more preferably from about 1% to about 5%, by weight of the foaming concentrate composition.

Water

The present compositions comprise water at a level of from about 0% to about 99%, preferably from about 50% to about 95%, and more preferably from about 75% to about 90%, by weight of the foaming concentrate composition.

Additional Optional Ingredients

The present compositions can further comprise additional optional ingredients. Suitable additional optional ingredients include perfume, preservatives, chelants, sensates (e.g. menthol), desquamation actives, anti-acne actives, anti-wrinkle/anti-atrophy actives, anti-oxidants/radical scavengers, flavonoids, anti-inflammatory agents, anti-cellulite agents, topical anesthetics, tanning actives, skin lightening agents, skin soothing and healing actives, antimicrobial actives, sunscreen actives, visual skin enhancers, and the like. Such optional ingredients are described more fully in U.S. application Ser. No. 11/367,918, filed Mar. 3, 2006. Preferred additional optional ingredients include salicylic acid, pigments (e.g. mica and titanium dioxide), perfume, and skin sensates (e.g. menthol).

The compositions of the present invention will typically have a pH in the range of from about 3 to about 10, preferably from about 4 to about 9, and more preferably from about 5 to about 8. The pH of the present compositions can be adjusted by utilizing pH control agents such as citric acid, triethanolamine, sodium hydroxide, and the like.

Propellant

The aerosol product of the present invention comprises a propellant suitable for generating a foam of the concentrate composition upon dispensing. The total concentration of the propellant in the aerosol composition can include one or more propellants, the total propellant concentration typically ranging from about 1% to about 25%, preferably from about 2% to about 15%, more preferably from about 3% to about 10%, by weight of the composition.

Nonlimiting examples of suitable propellants include hydrocarbons, nitrogen, carbon dioxide, nitrous oxide, atmospheric gas, 1,1-difluoroethane (Hydrofluorocarbon 152A) supplied as Dymel 152A by Dupont, dimethylether ("DME"), and mixtures thereof. Preferred are the hydrocarbon propellants and hydrocarbon/dimethylether propellant blends, specific examples of which include propane, butane, isobutane and dimethylether. Most preferred is a hydrocarbon propellant containing a mixture of propane and isobutane or a mixture of propane, isobutane and dimethylether, specific examples of which include Aeron A-46 and Aeron A-70 (both are commercially available from Diversified CPC alone or blended with dimethylether). One of ordinary skill in the art of aerosol products recognizes that geographic governmental regulations can dictate levels of volatile organic chemicals such as propellants.

Package

The foaming concentrate composition and propellant of the present invention are packaged in a package comprising a container and a powder valve comprising an orifice having an orifice diameter of at least about 0.026 inches (660 µm).

Powder Valve

The package of the present invention comprises a powder valve that comprises an orifice having an orifice diameter of at least about 0.026 inches (660 μm), preferably at least about 0.027 inches (685 μm), and more preferably at least about 0.030 inches (762 μm). As used herein, the term "orifice diameter" means the maximum distant between opposite sides of the orifice opening. The powder valve will have one, two, three, four or more orifices on a valve stem, preferably one or two orifices. The diameter of each of the orifices of the present invention can have the same or different orifice diameter. Preferably the orifices have the same orifice diameter. The orifices can be in the form of a variety of shapes, such as circular, square, rectangular, oval, trapezoidal, and the like. Orifice shape can be selected based upon the shape of the particulate material used in the foaming concentrate composition. Preferably, the orifice is circular or rectangular in shape and the particulate material is generally spherical or oval in shape. The orifice preferably has an opening area of at least about 0.340 mm$^2$, more preferably at least about 0.400 mm$^2$, and more preferably at least about 0.450 mm$^2$.

In a conventional form of aerosol valve the upper horizontal surface, when the aerosol valve is closed, is urged upwardly into sealing relation against the valve sealing gasket by the spring acting on the valve body. One or more orifices in the valve stem are positioned above the lower surface of the valve gasket when the valve is in the closed position. When the valve is opened by pressing the button, the valve stem moves downwardly and its one or more orifices will move to a position below the gasket. The foaming concentrate composition in the aerosol container can then, under the influence of propellant, pass upwardly through the orifice into the valve stem and then be dispensed through a nozzle.

A powder valve will typically have the orifice(s) of the valve stem positioned above the sealing gasket in the closed position, or positioned in at least the upper half of the sealing gasket in the closed position, to keep the particulate material from causing a leak between the sealing gasket and the orifice. Conventional aerosol valves typically have issues with clogging when dispensing compositions that contain particulate material of any size. The powder valve of the present invention helps to prevent clogging of the aerosol product by wiping the orifice opening against the sealing gasket as the valve moves from an open position to a closed position. In addition, powder valves will typically have different shapes in the valve body to keep particulate material from building up on the sealing surface. Non-limiting examples of suitable powder valve configurations are described in detail in U.S. Pat. Nos. 3,773,064, 5,975,378 and 6,394,321.

One embodiment of a powder valve of the present invention in a closed position is represented in the FIGURE. The powder valve assembly 10 generally includes a dip tube 12, a valve housing 14, a valve closing coil spring 16, and a valve body 18. The valve body 18 has a hollow valve stem 20 extending upwardly therefrom and containing at least one orifice 22 leading into the interior of the valve stem 20. A sealing gasket 24, preferably made of a resilient material such as rubber, surrounds the valve stem 20 and seals the orifice 22 when the powder valve is in a closed position, as shown. An actuator 26 having a nozzle 28 is attached to the top of the valve stem 20. When the actuator 26 is depressed downwardly against the force of the coil spring 16, the orifice 22 passes below the sealing gasket 24 and the foaming concentrate composition within the container can pass up through the dip tube 12, into the valve body 18, through the orifice 22, into the valve stem 20, into the actuator 26, and then finally dispensed out through the nozzle 28. When the actuator 26 is released, the coil spring 16 pushes the valve stem 20 and orifice 22 upwardly against the sealing gasket 24, wiping any remaining foaming concentrate composition away from the orifice 22 of the valve stem 20 to prevent clogging of the orifice 22 and blocking the flow of the foaming concentrate composition.

Container

The container of the present invention can be a variety of aerosol containers known in the art. The container can be a single chamber container or a barrier container. Non-limiting examples of single chamber containers include plastic, glass, aluminum or steel containers that may be unlined or lined with materials such as epoxy phenolics, organosols and polyamide imides. In such single chamber containers, the foaming concentrate composition and propellant are combined in the single chamber. Barrier containers keep the foaming concentrate composition physically separate from the propellant within the container. Non-limiting examples of barrier containers include a piston container and a bag-in-can container.

Actuator

The actuators of the present invention can be a variety of actuators known in the art. The actuator can be a front hinged, rear hinged or non-hinged actuator, as long as the actuator is properly matched with the valve stem. Non-limiting examples of suitable hinged actuators include those available from Seaquist Perfect Dispensing under the trade names S30, S25, S20 and Allegra for upright containers and under the trade names S16 and S4 for inverted containers. Non-hinged actuators can be preferred in the present invention as they tend to exhibit less lateral pressure during actuation of the aerosol product. Non-limiting examples of suitable non-hinged actuators include those available from Precision Valve under the trade names City Spout, Hercules Spout, and Iris, and those available from Seaquist Perfect Dispensing under the trade name S2.

EXAMPLES

The following are non-limiting examples of the foaming aerosol compositions of the present invention. The following reference list corresponds to the ingredients listed in the tables below, according to the superscript numerals.

[1] Synthetic layered silicate available from Southern Clay Products, Inc.
[2] Mixture of bentonite and xanthan gum available from Süd-Chemie.
[3] High purity surface modified montmorillonite available from Southern Clay Products, Inc.
[4] CARBOPOL AQUA SF-1 available from Noveon, Inc.
[5] ACULYN 28 available from Rohm & Haas.
[6] Available from P&G Chemicals.
[7] Available from Stepan.
[8] Available from Rhodia.
[9] Available from Croda.
[10] Available from Degussa.
[11] Pigment available from Englehard.
[12] Oxidized polyethylene beads having a particle size of less than 420 μm (sieved through a 40 mesh). Available from Honeywell.
[13] Micronized polypropylene beads having a particle size of less than 300 μm (sieved) available from Micro Powders, Inc.
[14] High density oxidized polyethylene colored beads having a particle size of less than 300 μm (sieved) available from Accutech LLC.
[15] Low density polyethylene beads having a particle size of less than 420 μm (sieved through a 40 mesh) available from Accutech LLC.

[16] High density oxidized polyethylene colored beads having a particle size of less than 600 μm (sieved) available from Accutech LLC.
[17] Low density polyethylene beads having a particle size of less than 590 μm (sieved through a 30 mesh) available from Accutech LLC.
[18] METHOCEL K15MS available from Amerchol
[19] SUPERWHITE PROTOPET available from Crompton
[20] HYDROBRITE 1000PO available from Crompton

|  | Foaming Concentrate | | | | | | |
|---|---|---|---|---|---|---|---|
|  | 1 | 2 | 3 | 4 | 5 | 6 | 7 |
| Water | QS | QS | QS | QS | QS | QS | QS |
| Laponite XLG[1] |  |  |  | 0.50 | 0.3 | 0.2 |  |
| Optigel WM[2] |  |  |  |  |  |  | 0.2 |
| Mineral Colloid MO[3] |  |  | 0.5 |  |  |  |  |
| Acrylates/C10-30 alkyl acrylate crosspolymer[4] |  | 0.4 |  |  |  |  |  |
| Acrylates/Beheneth-25 Methacrylate Copolymer[5] |  |  |  | 0.5 | 0.3 | 0.2 | 0.2 |
| Hydroxypropylmethylcellulose |  |  |  |  | 0.1 | 0.05 | 0.05 |
| Sodium Laureth Sulfate[6] | 4.0 |  |  |  |  |  |  |
| Sodium C14-16 Olefin Sulfonate[7] |  |  | 6.0 |  |  |  |  |
| Sodium Trideceth Sulfate[8] |  | 1.5 |  | 1.5 |  |  |  |
| Sodium Myristoyl Sarcosinate[9] |  | 3.0 |  | 1.5 |  |  |  |
| Sodium Hydroxide |  |  |  |  |  |  |  |
| Myristic Acid |  |  |  |  |  |  | 2.0 |
| Lauric Acid |  |  |  |  | 2.0 | 2.0 | 2.0 |
| Triethanolamine |  |  |  |  | to pH ~6 | to pH ~7 | to pH ~8 |
| Sodium Lauroamphoacetate[8] |  |  |  | 3.0 |  |  |  |
| Cocamidopropyl Betaine[10] | 4.0 | 4.5 | 4.0 |  | 2.0 | 2.0 | 4.0 |
| PEG 100 |  |  |  | 0.2 |  |  |  |
| Glycerin | 4.0 | 4.0 |  | 2.0 | 2.0 | 2.0 | 2.0 |
| Sorbitol |  |  |  | 2.0 | 2.0 | 2.0 | 2.0 |
| Menthol |  |  |  |  | 0.15 | 0.15 | 0.10 |
| Salicylic Acid |  |  | 0.5 |  |  |  |  |
| Fragrance |  | 0.15 |  | 0.1 | 0.1 | 0.1 | 0.1 |
| Preservative |  | 0.3 |  | 0.3 | 0.3 | 0.3 | 0.3 |
| Mica and Titanium Dioxide[11] |  |  |  |  |  |  | 0.1 |
| A-C Wax 395-A[12] |  |  | 5.0 |  |  |  |  |
| PropylTex 50[13] |  | 1.0 |  | 2.0 |  | 2.0 |  |
| Accuscrub BU310[14] | 1.0 | 1.0 |  |  | 2.0 |  |  |
| Accuscrub WT06 LDPE sieved at 40 mesh (420 micron)[15] |  |  |  |  |  |  | 2.0 |
| Citric Acid | to pH 5.5-6 | to pH 5.5-6 | to pH 5.5-6 | to pH 5.5-6 |  |  |  |
| Filling/Packing: |  |  |  |  |  |  |  |
| Foaming Concentrate | 95.00 | 92.00 | 95.00 | 95.00 | 95.00 | 95.00 | 95.00 |
| Propellant: |  |  |  |  |  |  |  |
| Dymel 152A |  | 3.0 |  |  |  |  |  |
| A-70/DME(45:55) | 5.0 |  | 5.0 | 5.0 |  |  |  |
| A-70 |  |  |  |  |  |  | 5.0 |
| A-46 |  | 5.0 |  |  | 5.0 | 5.0 |  |

The foaming concentrate compositions of Examples 1-7 are made as follows. If a clay suspension agent is present in the composition, the clay is added to deionized water and mixed until fully hydrated. Then hydrophobic conditioning agents, hydrophilic conditioning agents (should be in liquid form when added), additional suspension agents, and/or fatty acids are added, if present in the composition. If fatty acids or petrolatum are present, gentle heat may be applied to melt the fatty acids or more easily incorporate the petrolatum. If the pH is less than the desired target, then a pH control agent, typically a base such as triethanolamine or sodium hydroxide, is added to raise the pH to the desired target. If the pH is greater than the desired target, then a pH control agent, typically an acid such as citric acid, is added to lower the pH to the desired target. Any additional ingredients, such as particulate materials, preservatives, fragrance, colorants/pigments, and the like, are then added.

The foaming concentrate compositions of Examples 1-7 are then each filled into polyamide imide lined aluminum cans available from CCL Industries, Inc. A powder valve is inserted into each of the liquid-filled cans and then crimped. The powder valve used has a valve stem with a single orifice selected from a circular orifice having an orifice diameter of 0.030" (available from Precision Valve), a rectangular orifice having dimensions of 0.027" high by 0.045" wide (i.e. an orifice diameter of 0.045"), or a laser-cut square orifice having dimensions of 0.030" high by 0.030" wide (i.e. an orifice diameter of 0.030"). Propellant is then charged at the desired amount into each can. An actuator is then installed onto each can to allow for dispensing of the foaming concentrate composition. The actuator is available from SeaquistPerfect Dispensing under the trade name S-30.

|  | Foaming Concentrate | | | |
|---|---|---|---|---|
|  | 8 | 9 | 10 | 11 |
| Water | QS | QS | QS | QS |
| Palmitic Acid | 6.0 | 8.0 | 7.0 | 10.0 |
| Myristic Acid | 1.5 |  | 2.0 | 1.0 |
| Lauric Acid |  | 1.0 |  |  |
| Triethanolamine | to pH 7-9 | to pH 7-9 | to pH 7-9 | to pH 7-9 |
| Propylene Glycol Monoisostearate | 2.0 |  |  |  |
| Oleth-20 |  | 1.5 | 1.5 | 1.5 |
| Glycerin | 2.0 | 2.0 | 2.0 | 2.0 |
| Sorbitol | 2.0 | 2.0 | 2.0 | 0.5 |
| Menthol | 0.15 | 0.15 | 0.10 |  |
| PEG-14M | 0.1 |  | 0.05 | 0.15 |
| Fragrance | 0.1 | 0.1 | 0.1 | 0.1 |
| Preservative | 0.3 | 0.3 | 0.3 | 0.3 |
| Mica and Titanium Dioxide[11] |  |  | 0.1 |  |
| Propyltex 50[13] |  | 2.0 |  |  |
| Accuscrub BU310[14] | 2.0 |  |  |  |
| Accuscrub WT06 LDPE sieved at 40 mesh (420 micron)[15] |  |  | 2.0 | 2.0 |
| Post Foaming Aids: |  |  |  |  |
| Isobutane | 0.9 | 0.9 | 0.9 | 0.5 |
| Isopentane | 2.1 | 2.1 | 2.1 | 1.5 |
| Pentane |  |  |  | 1.0 |

The foaming concentrate compositions of Examples 8-11 are made by the same process as described above for Examples 1-7 with the exception that the composition is chilled to below 5° C. prior to addition of the Post Foaming Aids.

The foaming concentrate compositions of Examples 8-9 are then filled under chilled conditions into piston cans available from CCL Industries, Inc. or U.S. Can Company. A powder valve is inserted into each of the liquid-filled cans and then crimped. The powder valve used has either a valve stem with a single orifice having an orifice diameter of 0.030" (available from Precision Valve Corp.). Propellant is then filled through the bottom of the can to a fixed pressure to provide a means of evacuation. An actuator is then installed onto each can to allow for dispensing of the foaming concentrate composition. The actuator is available from Precision Valve Corp. under the trade name Hercules Spout, which is a non-hinged actuator.

The foaming concentrate compositions of Examples 10-11 are then filled under chilled conditions into bag-in-can containers available from U.S. Can Company under the trade name SEPRO®. A powder valve is inserted into each of the liquid-filled cans and then crimped. The powder valve used has either a valve stem with a single orifice having an orifice diameter of 0.030" (available from Precision Valve Corp.). Propellant is then filled through the bottom of the can to a fixed pressure to provide a means of evacuation. An actuator is then installed onto each can to allow for dispensing of the foaming concentrate composition. The actuator is available from Precision Valve Corp. under the trade name Hercules Spout, which is a non-hinged actuator.

The following table includes Examples 12 and 13 of the present invention, as well as Comparative Examples A, B, C and D. The products are made according to the process described above for Examples 1-7, using an actuator available from Precision Valve Corp. under the trade name City Spout. Each product example is evaluated as to whether the valve of the product becomes clogged or seeps due to the particulate materials in the foaming concentrate compositions.

|  | Foaming Concentrate | | | | | |
|---|---|---|---|---|---|---|
|  | 12 | A | 13 | B | C | D |
| Water | QS | QS | QS | QS | QS | QS |
| Laponite XLG[1] | 0.50 | 0.50 | 0.3 | 0.3 | 0.50 | 0.50 |
| Acrylates/Beheneth-25 Methacrylate Copolymer[5] | 0.5 | 0.5 | 0.3 | 0.3 | 0.5 | 0.5 |
| Hydroxypropylmethylcellulose |  |  | 0.1 | 0.1 |  |  |
| Sodium Trideceth Sulfate[8] | 1.5 | 1.5 |  |  | 1.5 | 1.5 |
| Sodium Myristoyl Sarcosinate[9] | 1.5 | 1.5 |  |  | 1.5 | 1.5 |
| Lauric Acid |  |  | 2.0 | 2.0 |  |  |
| Triethanolamine |  |  | to pH 6-7 | to pH 6-7 |  |  |
| Sodium Lauroamphoacetate[8] | 3.0 | 3.0 |  |  | 3.0 | 3.0 |
| Cocamidopropyl Betaine[10] |  |  | 2.0 | 2.0 |  |  |
| Glycerin | 2.0 | 2.0 | 2.0 | 2.0 | 2.0 | 2.0 |
| Sorbitol | 2.0 | 2.0 | 2.0 | 2.0 | 2.0 | 2.0 |
| Menthol |  |  | 0.15 | 0.15 |  |  |
| Fragrance | 0.1 | 0.1 | 0.1 | 0.1 | 0.1 | 0.1 |
| Preservative | 0.3 | 0.3 | 0.3 | 0.3 | 0.3 | 0.3 |
| Petrolatum[19] |  |  |  |  |  | 7.0 |
| Mineral Oil[20] |  |  |  |  |  | 3.0 |
| Accuscrub BU310[14] | 2.0 |  |  |  | 2.0 |  |
| Accuscrub BU301[16] |  | 2.0 |  |  |  |  |
| Accuscrub WT06 LDPE sieved at 40 mesh (420 micron)[15] |  |  | 2.0 |  |  |  |
| Accuscrub WT06 LDPE sieved at 30 mesh (590 micron)[17] |  |  |  |  | 2.0 |  |
| Citric Acid | to pH 5.5-6 | to pH 5.5-6 |  |  | to pH 5.5-6 | to pH 5.5-6 |

-continued

|  | Foaming Concentrate | | | | | |
| --- | --- | --- | --- | --- | --- | --- |
|  | 12 | A | 13 | B | C | D |
| Fill/Packing: | | | | | | |
| Phase A Concentrate | 95.00 | 95.00 | 95.00 | 95.00 | 95.00 | 95.00 |
| Propellant: | | | | | | |
| A-70 | 5.0 | 5.0 | | | 5.0 | 5.0 |
| A-46 | | | 5.0 | 5.0 | | |
| Valve: | | | | | | |
| Type of Valve | Powder | Powder | Powder | Powder | Conventional | Conventional |
| Number of Orifices | 1 | 1 | 1 | 1 | 2 | 2 |
| Diameter of Each Orifice | 0.030" | 0.030" | 0.030" | 0.024" | 0.020" | 0.020" |
| Ratio of Maximum Particle Size to Orifice Diameter | 0.39 | 0.79 | 0.55 | 0.97 | 0.59 | NA |
| Clogs or seeps during use? | NO | YES | NO | YES | YES | NO |

The results in the table above show that in order to dispense foaming concentrate compositions containing relatively large particulate materials, the type of valves and orifice diameters, as well as the ratio of maximum particle size to orifice diameter, can be important considerations in achieving an aerosol product having a valve that does not clog or seep when dispensing a foaming concentrate composition containing relatively large particulate materials. It is also note worthy that emulsified droplets of a mixture of petrolatum and mineral oil (Example D) at a level of 10% will not clog a conventional valve.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol product comprising:
   (a) a foaming concentrate composition comprising:
      (i) a surfactant; and
      (ii) from about 0.1% to about 10%, by weight of said foaming concentrate composition, of particulate material; wherein said foaming concentrate composition comprises at least about 0.1%, by weight of said foaming concentrate composition, of particulate material having a particle size of at least about 150 µm;
   (b) a propellant; and
   (c) a package containing said foaming concentrate composition and said propellant; wherein said package comprises a container and a powder valve comprising a valve stem; wherein said valve stem comprises an orifice having an orifice diameter of at least about 660 µm; wherein said orifice is sealed when said valve is in a closed position.

* * * * *